United States Patent
Kim et al.

(10) Patent No.: US 12,077,779 B2
(45) Date of Patent: Sep. 3, 2024

(54) FEEDER CELL AND METHOD FOR GROWING GAMMA DELTA T CELLS BY USING SAME

(71) Applicant: THE CATHOLIC UNIVERSITY OF KOREA INDUSTRY-ACADEMIC COOPERATION FOUNDATION, Seoul (KR)

(72) Inventors: Tai Gyu Kim, Seoul (KR); Hyun Jung Sohn, Seoul (KR); Hyun Woo Cho, Gyeonggi-do (KR); Su Yeon Kim, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 631 days.

(21) Appl. No.: 16/349,225

(22) PCT Filed: Nov. 10, 2017

(86) PCT No.: PCT/KR2017/012701
§ 371 (c)(1),
(2) Date: May 10, 2019

(87) PCT Pub. No.: WO2018/088829
PCT Pub. Date: May 17, 2018

(65) Prior Publication Data
US 2019/0284532 A1    Sep. 19, 2019

(30) Foreign Application Priority Data
Nov. 11, 2016 (KR) .................. 10-2016-0150338

(51) Int. Cl.
| | |
|---|---|
| A61K 48/00 | (2006.01) |
| A61K 35/17 | (2015.01) |
| A61K 39/39 | (2006.01) |
| A61K 51/10 | (2006.01) |
| C07K 14/705 | (2006.01) |
| C12N 5/073 | (2010.01) |
| C12N 5/0783 | (2010.01) |
| C12N 5/09 | (2010.01) |
| C12N 5/10 | (2006.01) |
| G01N 33/50 | (2006.01) |
| G01N 33/569 | (2006.01) |

(52) U.S. Cl.
CPC ............ *C12N 5/0638* (2013.01); *A61K 35/17* (2013.01); *A61K 39/39* (2013.01); *A61K 51/1042* (2013.01); *C07K 14/70532* (2013.01); *C07K 14/70578* (2013.01); *C07K 14/70596* (2013.01); *C12N 5/0603* (2013.01); *C12N 5/0636* (2013.01); *C12N 5/0694* (2013.01); *C12N 5/10* (2013.01); *G01N 33/505* (2013.01); *G01N 33/56972* (2013.01); *C12N 2501/2302* (2013.01); *C12N 2501/51* (2013.01); *C12N 2501/515* (2013.01); *C12N 2501/52* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 10,557,117 B2 * | 2/2020 | Maher ..................... | A61P 35/02 |
| 10,968,426 B2 * | 4/2021 | Meissner ............. | C12N 5/0696 |
| 2006/0034810 A1 * | 2/2006 | Riley ...................... | A61P 37/04 |
| | | | 424/93.21 |
| 2019/0309259 A1 * | 10/2019 | Meissner ............... | C12N 15/86 |

FOREIGN PATENT DOCUMENTS

| | | |
|---|---|---|
| WO | 2016/081518 A2 | 5/2016 |
| WO | 2016/087871 A1 | 6/2016 |

OTHER PUBLICATIONS

Figueiredo C, Blasczyk R. A future with less HLA: potential clinical applications of HLA-universal cells. Tissue Antigens. 2015;85:443-449.*
Kim et al., The ABCs of artificial antigen presentation. Nat Biotechnol. 2004;22:403-410.*
Shimizu et al., Production of human cells expressing individual transferred HLA-A,-B,-C genes using an Hla-A,B,-C null human cell line. J Immunol. 1989; 142:3320-3328.*
Marsden et al., Chem. Soc. Rev., 2011, pp. 1572-1585; Model systems for membrane fusion.*
Hong et al., Antigen Presentation by Individually Transferred HLA Class I Genes in HLA-A, HLA-8, HLA-C Null Human Cell Line Generated Using the Multiplex CRISPR-Cas9 System. J Immunether 2017 pp. 201-210.*
Zha et al., Beta-2 microglobulin knockout K562 cell-based artificial antigen presenting cells for ex vivo expansion of T lymphocytes Immunotherapy 2019 pp. 967-982.*
International Search Report and Written Opinion. Issued by the International Searching Authority (KR) in Application No. PCT/KR2017/012701. Feb. 12, 2018. 15 pages.
Sheridan, Brian S., and Joshua J. Obar. "Vγ9Vδ2 T cells: triple costimulation goes the distance." Journal of leukocyte biology 99.4 (2016): 515-517.

(Continued)

*Primary Examiner* — Maria G Leavitt
(74) *Attorney, Agent, or Firm* — Meunier Carlin & Curfman LLC

(57) ABSTRACT

The present invention relates to a novel feeder cell and a method for growing gamma delta T cells using the same. More specifically, a large amount of gamma delta T cells may be grown in vitro with high purity and without simulation of a T cell receptor by using a feeder cell into which costimulatory molecules are introduced and a low concentration of IL-2, differentiation into central memory cells may be possible when stimulated, activity by the feeder cell, and cytolytic against tumour cells is provided.

3 Claims, 15 Drawing Sheets

Specification includes a Sequence Listing.

(56) References Cited

OTHER PUBLICATIONS

Willoughby, Jane E., et al. "Differential impact of CD27 and 4-1BB costimulation on effector and memory CD8 T cell generation following peptide immunization." The Journal of Immunology 193.1 (2014): 244-251.

Sanchez-Paulete, Alfonso R., et al. "Deciphering CD137 (4-1BB) signaling in T-cell costimulation for translation into successful cancer immunotherapy." European journal of immunology 46.3 (2016): 513-522.

Cho, Hyun-Woo, et al. "Triple costimulation via CD80, 4-1BB, and CD83 ligand elicits the long-term growth of Vγ9Vδ2 T cells in low levels of IL-2." Journal of leukocyte biology 99.4 (2016): 521-529.

Office Action dated Jun. 19, 2019, received in connection with Korean Patent Application No. 10-2016-0150338.

Suhoski, Megan et al. "Engineering Artificial Antigen-presenting Cells to Express a Diverse Array of Co-stimulatory Molecules," NIH Public Access Author Manuscript; available in PMC Feb. 24, 2014.

\* cited by examiner

[Diagram of stimulation of feeder cells in the presence of zoledronic acid and IL-2]

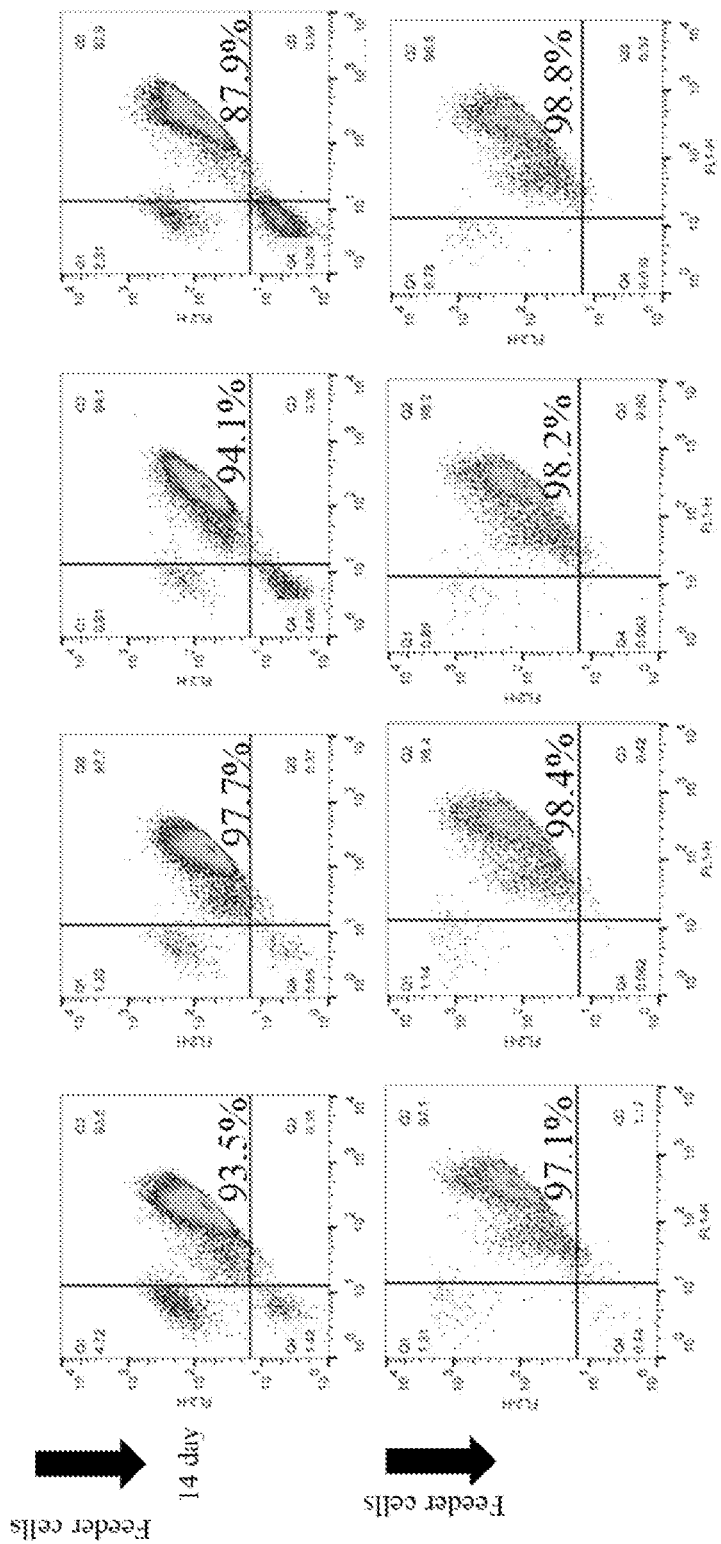
FIG. 6_continued

[Remaining alpha beta T cells in the absence or presence of T cell receptor stimulation]

FEEDER CELL AND METHOD FOR GROWING GAMMA DELTA T CELLS BY USING SAME

BACKGROUND

1. Field of the Invention

The present invention relates to novel feeder cells into which a costimulatory molecule is introduced, and a method of mass-proliferating high purity gamma-delta (γδ) T cells in vitro using the same in the presence of a low concentration of IL-2 without T cell receptor stimulation.

2. Discussion of Related Art

Recently, significant processes for understanding the role of human γδ T cells have been made in immune responses against infections, tumors and autoimmune diseases. Human γδ T cells expressing Vγ9Vδ2 TCR have been known as the major subset which can be activated in peripheral blood in a human leukocyte antigen (HLA)-unrestricted manner by small non-peptidic phosphoantigens. Vγ9Vδ2 T cells include NKG2D and ULBP4, which are expressed in tumor cells, and are capable of recognizing their ligands, thereby exhibiting strong cytotoxicity against tumor cells. In addition, both manipulations of the activation of Vγ9Vδ2 T cells in vivo and the activation of autologous Vγ9Vδ2 T cells expanded ex vivo and adoptively transferred are being considered as new immunotherapeutic approaches. Many protocols for the ex vivo expansion of Vγ9Vδ2 T cells using a natural antigen, i. e., isopentenyl pyrophosphate, against human Vγ9Vδ2 T cells have been developed. Particularly, Correia et al. have reported that a phosphoantigen alone cannot activate Vγ9Vδ2 T cells, and the addition of a high concentration of IL-2 is significant for completing the activation of Vγ9Vδ2 T cells. More significantly, mature dendritic cells pretreated with aminobisphosphate are able to induce the expansion of high-purity Vγ9Vδ2 T cells in peripheral blood mononuclear cells (PBMCs), which does not correspond to a conventional culture protocol. Since the mature dendritic cells express a variety of costimulatory molecules, including CD80, CD83 and 4-1BBL, data on these molecules shows that signaling using a large number of costimulatory receptors activates Vγ9Vδ2 T cells. Even though it has been proven that various costimulatory molecules including CD80 and a 4-1BB ligand (4-1BBL) participate in promotion of the proliferation and survival of peripheral Vγ9Vδ2 T cells, the functions of CD83 and its ligand for the activation of γδ T cells are little known.

SUMMARY OF THE INVENTION

An object of the present invention is directed to providing feeder cells that are able to express a costimulatory molecule group and stimulate γδ T cells.

Another object of the present invention is also directed to providing a composition and method for proliferating high purity γδ T cells in vitro using the feeder cells in the presence of a low concentration of IL-2 without T cell receptor stimulation.

To attain the objects of the present invention, the present invention provides feeder cells for stimulating γδ T cells, which express a costimulatory molecule group including 4-1BBL, CD80 and CD83, but do not express HLA.

The present invention provides a composition for in vitro proliferating γδ T cells including the feeder cells for stimulating γδ T cells.

The present invention also provides a method of in vitro proliferating γδ T cells, which includes ex vivo co-culturing the feeder cells for stimulating γδ T cells and γδ T cells without T cell receptor stimulation.

According to the present invention, high purity γδ T cells can be mass-proliferated in vitro by stimulating γδ T cells using feeder cells in the presence of a low concentration of IL-2 without T cell receptor stimulation, and the γδ T cells can differentiate into central memory cells and have cytolytic activity against tumor cells.

DETAILED DESCRIPTION OF EXEMPLARY EMBODIMENTS

Figure 1:
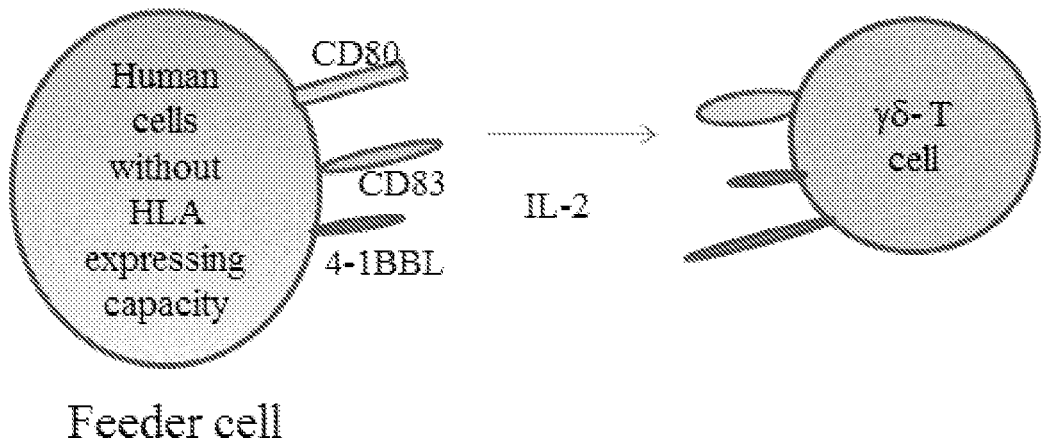
FIG. 1 is a diagram illustrating a feeder cell expressing costimulatory molecules for in vitro proliferating γδ T cells according to the present invention.

The inventors investigated the roles of costimulatory molecules including CD83 for the survival, proliferation and cytokine formation of human γδ T cells in vitro. First, since K562 cells do not express HLA molecules, but have an advantage of expressing adhesion molecules, for example, ICAM, LFA-3 and NKG2D ligands and MHC class I-related chain A, a stable K562-based transformant expressing a costimulatory molecule group consisting of 4-1BBL/CD80/CD83 or a costimulatory molecule group consisting of 4-1BBL/CD80/CD83/CD40L was prepared. These transformants were further transduced to raise the expression rate(s) of Fc receptor(s) such as CD32 and/or CD64.

It has been known that the 4-1BB/4-1BBL interaction is independent from B7/CD28 signaling, and increases the survival of cells activated in vivo. Particularly, the participation of CD83 noticeably upregulated during the maturation of dendritic cells has been known to inhibit apoptosis, thereby improving the long-term survival of T cells.

In addition, stimulation may be performed by additionally transferring costimulatory molecules such as γδ T cell-stimulatory molecules, i.e., MIC and ULBP to the cells. The inventors confirmed that K562-based feeder cells allow the long-term growth of functional effector-memory Vγ9Vδ2 T cells, and the proliferation rate of high purity Vγ9Vδ2 T cells is increased in vitro in the presence of a low concentration of IL-2 without T cell receptor stimulation.

From the above-described result, it was found that the costimulatory signals involved in the activation and survival of human γδ T cells eventually improve γδ T cell-based immunotherapeutic strategies for cancer, infections and autoimmune diseases.

Therefore, the present invention relates to feeder cells for stimulating γδ T cells, which express a costimulatory molecule group including 4-1BBL, CD80 and CD83 and do not express HLA.

The term "feeder cell" used herein refers to artificially manufactured antigen-presenting cells, and non-immune cells modified to express an immune molecule. Feeder cells expressing an MHC class I or II (MHC I or II) molecule alone or in combination with other accessory molecules (costimulatory molecules and/or adhesion molecules) may be used to study various aspects of T cell-activating cells which can be easily cultured, such as tumor cells or a fibroblast cell line in vivo. For the purpose of the present invention, the feeder cell means a cell in which cDNA of costimulatory molecules is introduced into any one of human cells without HLA expressing capacity, such as K562 cells and recombinant HEK 293T cells from which an HLA gene is artificially removed, but the present invention is not limited thereto.

The feeder cells of the present invention are prepared from cells without an HLA expressing capacity, and prepared by introducing respective nucleic acids encoding a costimulatory molecule group including costimulatory molecules such as 4-1BBL, CD80 and CD83, or a costimulatory molecule group including 4-1BBL, CD80, CD83 and CD40L into cells having no HLA expressing capacity or from which HLA expressing capacity is removed. Compared with conventional feeder cells, the feeder cells of the present invention are able to stimulate cells without the stimulation with an immunostimulatory ligand, that is, a T cell receptor.

Therefore, the feeder cells may mass-produce high purity γδ T cells in vitro only with the combination of costimulatory molecules without T cell receptor stimulation.

In the feeder cells, Fc receptor(s), that is, CD32 and/or CD64, other than the costimulatory molecules, are/is further transduced to increase the expression rate(s) of CD32 and/or CD64.

The feeder cells may stimulate any one type of naive γδ T cells isolated from human PBMCs and enriched γδ T cells obtained by stimulating human PBMCs with zoledronic acid.

The naive γδ T cells may be isolated from human PBMCs by FACS sorting or using anti-γδ antibody-conjugated microspheres, thereby exhibiting Vγ9Vδ2 subsets and having CD83/4-1BBL/anti-CD28 signals.

The enriched γδ T cells may be obtained by stimulating human PBMCs with zoledronic acid, or by being isolated by FACS sorting or using anti-γδ antibody-conjugated microspheres after stimulation with zoledronic acid. The enriched γδ T cells may exhibit Vγ9Vδ2 subsets the same as the naive γδ T cells, and have CD83/4-1BBL/anti-CD28 signals.

To provide antigenic specificity, the feeder cells of the present invention may be further transduced with nucleic acid(s) encoding any one or more antigens selected from the group consisting of a tumor antigen, a pathogenic antigen and an autoantibody.

The term "antigen" used herein is well known in the art, and includes an epitope, a peptide fragment of an antigen capable of binding to an MHC molecule, and an immunogen, as well as all molecules capable of binding to an antibody. In the present invention, as an antigen, a tumor antigen, a pathogenic antigen or an autoantibody (normal or pathological) may be used, but the present invention is not limited thereto.

The tumor antigen refers to a tumor-associated antigen (TAA), which is an antigen associated with a tumor. Examples of well-known TAAs include ovalbumin, survivin, gp75, gp1OO, MDM2, MART-1, MAGE-1, MAGE-3, tyrosinase, telomerase, her-2/neu, α-1 fetoprotein, G250, and NY-ESO-1. Partial peptide fragment sequences of TAAs binding to an MHC molecule include $Ova_{257}$ (SIINFEKL; SEQ ID NO: 25), tyrosinase-related protein 1455 ($Trp1_{455}$; TAPDNLGYA; SEQ ID NO: 26), $Trp2_{180}$ (SVYDFFVWL; SEQ ID NO: 27), $gp100_{25}$ ($gp100_{25}$; EGSRNQDWL; SEQ ID NO: 28), a MAGE 1 nonapeptide (EADPTGHSY; SEQ ID NO: 29), a MART-APL peptide (LAGIGILTV; SEQ ID NO: 30), a natural peptide (AAGIGILTV; SEQ ID NO: 31), and a PSA-1 peptide (FLTPKKLQCV; SEQ ID NO: 32). The sequences of additional tumor-associated peptides and antigens are known to those of ordinary skill in the art.

The pathogenic antigen refers to an organism or virus that causes a disease, or an attenuated derivative thereof. The term "pathogen" refers to any virus or organism, or an attenuated derivative thereof, which is involved in the occurrence of a disease. The pathogens may include bacterial, protozoan, fungal and viral pathogens, for example, Helicobacters such as *Helicobacter pylori*, *Salmonella* sp., *Shigella* sp., *Enterobacter* sp., and *Campylobacter* sp., various mycobacteria such as *Mycobacterium leprae* and *Mycobacterium tuberculosis*, *Bacillus anthracis*, *Yersinia pestis*, *Francisella tularensis*, *Brucella* sp., *Leptospira interrogans*, *Staphylococcus* sp. such as *S. aureus*, *Streptococcus* sp., *Clostridum* sp., *Candida albicans*, *Plasmodium* sp., *Leishmania* sp., *Trypanosoma* sp., human immunodeficient virus (HIV), hepatitis C virus (HCV), human papilloma virus (HPV), cytomegalovirus (CMV), HTLV, herpes viruses (e.g., Type 1 herpes simplex virus, Type 2 herpes simplex virus, Corona virus, Varicella-Joster virus, and Epstein-Barr virus), papilloma virus, influenza virus, hepatitis B virus, poliovirus, measles virus, mumps virus, and rubella virus, but the present invention is not limited thereto.

The autoantibody is an antinuclear antibody, an anti-γ globulin antibody, an antibody against a self-hemocyte component or an antibody against a self-organ, but the present invention is not particularly limited thereto. When the autoantibody is used as a foreign antigen, a CD4 T cell vaccine may induce potent antitumor immunity, and thus may be effective for overcoming potential immune tolerance to an auto-antigen expressed in normal tissue.

The term "costimulatory molecule" used herein is a material participating in the interaction between a receptor-ligand pair expressed on the surface of an antigen-presenting cell and a T cell, and to induce the expression and proliferation of a cytokine gene, two or more signals are required for resting T cells. A first signal is a signal imparting specificity, generated by the interaction between an MHC/peptide complex and a TCR/CD3 complex, and a second signal is antigen-nonspecific, and called a "costimulatory" signal. These signals are known to have activity provided by bone marrow-derived helper cells such as macrophages and dendritic cells. The costimulatory molecule performs complete activation of γδ T cells by mediating a costimulatory signal required under a normal physiological condition. In the present invention, as such costimulatory ligands, a combination of 4-1BBL, CD80 and CD83 or a combination of 4-1BBL, CD80, CD83 and CD40L is used.

The feeder cells of the present invention may be prepared by transducing costimulatory molecules into human cells without HLA expressing capacity or from which HLA expressing capacity is removed using a known transformation technique. According to an exemplary embodiment of the present invention, costimulatory molecules may be transduced into K562 cells.

A nucleic acid encoding the costimulatory molecule may be DNA or RNA.

Preferably, 4-1BBL may be a human or mouse-derived nucleic acid sequence, for example, a base sequence set forth in SEQ ID NO: 1, but the present invention is not limited thereto.

CD80 may be a human or mouse-derived nucleic acid sequence. For example, CD80 may be a base sequence set forth in SEQ ID NO: 2, but the present invention is not particularly limited thereto.

CD83 may be a human or mouse-derived nucleic acid sequence, for example, a base sequence set forth in SEQ ID NO: 3, but the present invention is not particularly limited thereto.

CD40L may be a human or mouse-derived nucleic acid sequence, for example, a base sequence set forth in SEQ ID NO: 4, but the present invention is not particularly limited thereto.

When DNA is selected as a nucleic acid encoding the costimulatory molecule, it may be provided to human cells which have no HLA expressing capacity or from which HLA expressing capacity is removed in a form of being inserted into a vector.

The term "vector" used herein means a nucleic acid molecule capable of delivering a different nucleic acid linked to the nucleic acid itself. There is a type of vector, called "plasmid," which is a circular double-stranded DNA loop capable of ligating an additional DNA segment. Another type of vector is a viral vector capable of ligating an additional DNA segment with a viral genome. Some vectors can be self-replicated in a host cell when being introduced into the host cell (e.g., a bacterial vector having a bacterial origin of replication and an episomal vector for a mammal). When being introduced into a host cell, a different vector (e.g., a non-episomal vector for a mammal) is able to be integrated into the genome of the host cell, and replicated with the host genome. In addition, some vectors may direct the expression of genes operably linked to each other. The vector of the specification refers to "recombinant expression vector" (or simply called "expression vector"). Generally, since an expression vector useful for a recombinant DNA technique is typically the most commonly-used vector type, the "plasmid" and "vector" may be used interchangeably. However, the present invention may include different types of expression vectors such as viral vectors providing equivalent functions (e.g., an adenovirus vector, an adeno-associated virus (AAV) vector, a herpes virus vector, a retrovirus vector, a lentivirus vector, and a baculovirus vector), and preferably, a retroviral vector.

The retrovirus is an RNA virus having a different life cycle from a lytic virus. In this regard, the retrovirus is an infectious agent that replicates through a DNA intermediate. When cells are infected by the retrovirus, the viral genome is converted into DNA due to reverse transcriptase. A DNA copy is used as a template for producing an encoded viral protein, which is necessary for a new RNA genome and the assembly of an infectious viral particle. There are many types of retroviruses, including all different families of retroviruses, for example, murine leukemia virus (MLV), human immunodeficiency virus (HIV), equine infectious anemia virus (EIAV), mouse mammary tumor-like virus (MMTV), Rouse sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), avian myeloblastosis virus-29 (MC29), avian erythromblastasis virus (AEV) and lentivirus. Detailed lists of the retroviruses are shown in Coffin et al. ("Retroviruses" 1997 Cold Spring Harbour Laboratory Press Eds: J M Coffin, S M Hughes, H E Varmus pp 758-763).

Transformation includes any method for introducing a nucleic acid into an organism, a cell, tissue or an organ, and may be carried out by selecting a suitable standard technique according to host cells as known in the art. Such methods include electroporation, plasma fusion, calcium phosphate ($CaPO_4$) precipitation, calcium chloride ($CaCl_2$) precipitation, stirring with silicon carbide fibers, agrobacteria-mediated transformation, PEG, dextran sulfate, and Lipofectamine, but the present invention is not limited thereto.

According to an exemplary embodiment of the present invention, each cDNA of each of the genes of human costimulatory molecules 4-1BBL, CD80, CD83 and CD40L is prepared through PCR amplification, and inserted into a retrovirus vector. The pcDNA3/CD80, pLXSN/4-1BBL, pcDNA3/CD83, and pcDNA3/CD40L are sequentially introduced into K562 cells for transformation.

The term "gamma-delta T cells" used herein may be used interchangeably with "γδ T cells."

The present invention also relates to a composition for in vitro proliferating γδ T cells including feeder cells for stimulating the γδ T cells.

The present invention also relates to a method of in vitro proliferating γδ T cells, which includes ex vivo co-culturing feeder cells for stimulating γδ T cells and γδ T cells without T cell receptor stimulation.

The γδ T cells used in the method of in vitro proliferating the γδ T cells according to the present invention may be any one of naive γδ T cells isolated from human PBMCs or enriched γδ T cells obtained by stimulating human PBMCs with zoledronic acid.

The co-culture of feeder cells and γδ T cells may be carried out without T cell receptor stimulation.

At this time, the T cell receptor stimulation means culturing in the presence of an anti-CD3 antibody or anti-γδ TCR antibody.

Therefore, the co-culture of feeder cells and γδ T cells are performed in a cell culture medium containing a low concentration of IL-2 in the absence of the anti-CD3 antibody or anti-γδ TCR antibody.

The cell culture medium may be a complete medium for animal cell culture. For example, Dulbecco's Modified Eagle's Medium (DMEM), Minimal Essential Medium (MEM), Basal Medium Eagle (BME), RPMI1640, F-10, F-12, α-Minimal Essential Medium (αMEM), Glasgow's Minimal Essential Medium (GMEM), or Iscove's Modified Dulbecco's Medium may be used, but the present invention is not limited thereto.

IL-2 may be added at a concentration of 20 to 100 IU/mL. Compared with a conventional method of in vitro proliferating γδ T cells, performed at a high concentration of 300 IU/mL or more, the method according to the present invention is performed with a considerably lower concentration of IL-2.

According to an exemplary embodiment of the present invention, the in vitro proliferation of γδ T cells may be performed by co-culturing feeder cells for stimulating γδ T cells, expressing a costimulatory molecule group consisting of 4-1BBL, CD80, CD83 and CD40L, and naive γδ T cells or enriched γδ T cells in the presence of 20 to 100 IU/mL of IL-2 without an anti-CD3 antibody or anti-γδ TCR antibody, or feeder cells for stimulating γδ T cells, expressing a costimulatory molecule group consisting of 4-1BBL, CD80 and CD83 and naive γδ T cells or enriched γδ T cells in the presence of 20 to 100 IU/mL of IL-2 without the anti-CD3 antibody or anti-γδ TCR antibody.

The simulation with feeder cells is repeated at intervals of 7 to 10 days, and the in vitro culture is able to be performed for 90 days or more, and more preferably, 14 to 100 days. Considering that the conventional method of in vitro proliferating γδ T cells is performed within a maximum of 14 days, long-term culture is possible.

The co-culture may be performed in a $CO_2$ incubator with a $CO_2$ flow amount of 5 to 15% at 35 to 37 r, but the present invention is not particularly limited.

In addition, according to an exemplary embodiment of the present invention, through the stimulation with feeder cells expressing 4-1BBL/CD80/CD83/CD40L or 4-1BBL/CD80/CD83, rather than the stimulation with zoledronic acid, high purity γδ T cells may be obtained, and the differentiation into central memory cells may last longer. Moreover, compared with the stimulation with feeder cells expressing 4-1BBL/CD80/CD83, the stimulation with feeder cells expressing 4-1BBL/CD80/CD83/CD40L enables long-term proliferation of γδ T cells, and thereby high purity γδ T cells may be obtained, and differentiation into central memory cells may last longer.

In addition, in the case of γδ T cells proliferated by the stimulation of feeder cells expressing 4-1BBL/CD80/CD83, an anti-apoptotic molecule is expressed such that cell proliferation is maintained for a long time, and the γδ T cells exhibit apoptotic capacity with respect to tumor cells.

Hereinafter, the present invention will be described in further detail with reference to examples according to the present invention, but the scope of the present invention is not limited by the following examples.

EXAMPLES

Example 1

In Vitro Proliferation of γδ T Cells Using Feeder Cells (Cells)

Human samples were reviewed and approved by the Institutional Review Board of Catholic University, Korea. PBMCs were collected according to leukapheresis, and centrifuged using a Ficoll-Paque (GE Healthcare) density gradient. $CD4^-$ T cells and $CD8^+$ T cells were isolated using $CD4^+$ T cell and $CD8^+$ T cell isolation kits (Miltenyi Biotec) according to magnetic cell sorting for positive selection (isolated to reach 95% or more purity). γδ T cells were isolated from PBMCs newly purified using an anti-TCRγ/δ MicroBead kit (Miltenyi Biotec) according to magnetic cell sorting (isolated to reach 60% or more purity). Particularly, to isolate Vγ9Vδ2 T cells (isolated to reach 95% or more purity), the γδ T cells were sorted using FACSAria (Becton Dickinson) so as to be further isolated into $CD3^+$ and $Vγ9^+$ subsets.

For cell surface staining, the cells were incubated with anti-TCRVγ9-PE (B3) and anti-CD3-FITC (OKT3) on ice for 30 minutes. A Burkitt's lymphoma cell line Daudi, an erythroid bone marrow cell line K562 and a leukemia cell line U937 were obtained from ATCC, and cultured in a complete medium. The complete medium was a 1640 RPMI (Lonza) medium containing 10% heat-inactivated FBS (Gibco), 2 mM L-glutamine (Lonza), 100 U/mL of penicillin (Lonza), and 100 μg/mL of streptomycin (Lonza).

(Establishment of Feeder Cells)

Human CD80, 4-1BBL and CD83 genes were amplified from cDNA through PCR, and cloned into 3.1-neo (Invitrogen) and a pLXSN retrovirus vector (Clontech). First, K32 was prepared by transducing CD80 into K562 cells. Then, K80/4-1BBL and K80/CD83 were produced by transducing 4-1BBL or CD83 into K80 cells. Finally, K80/4-1BBL/CD83 was produced by transducing CD83 into K80/4-1BBL. Human CD80 and 4-1BBL genes were cloned from a U937 cell line, and the CD83 gene was cloned from mature DC. pcDNA3/CD80 and/or pLXSN/4-1BBL and/or pcDNA3/CD83 plasmids were sequentially transformed into K562 cells using Nucleofector Kit V (Amaxa) according to the manufacturer's instructions. The transformants were cultured in the presence of 1 mg/mL of G-418 DISULPHATE (Duchefa Biochemie). The transformed cells were further selected by FACSAria. All artificial APCs were identified as a mycoplasma-free line, as determined by PCR (data not shown).

(FACS Analysis)

The following mAbs were used to test surface expression of costimulatory molecules and activation markers in K562 and Vγ9Vδ2 T cells: FITC-, PE-, Alexa Fluor 488-, APC-, or Cy5-conjugated mAbs: anti-CD3(OKT3), anti-TCRVδ2 (B6), anti-HLA-A,B,C(W6/32), anti-CD27(O323), anti-CD27(O323), anti-CD45RA(HI100), anti-CD32(FUN-2), anti-CD25(BC96), anti-CD69(FN50), anti-CD28(CD28.2), anti-CD86(IT 2.2), anti-137(4B4-1), anti-137L(5F4), anti-CD 83 (HB 15 e), anti-CD80(2D 10), anti-NKG2D(CD314), anti-TCRVγ9(B3), anti-TCRγ/6(B1), and anti-HLA-DR, DQ-PE Abs.

All antibodies were purchased from BioLegend or Ancell. Simply put, $1×10^6$ viable T cells in 100 μl of PBS (Lonza) were washed twice with 2% FBS-containing PBS. The cells stained with cell surface markers were fixed using 1% paraformaldehyde in PBS. Subsequently, the cells were analyzed using FACSCalibur (Becton Dickinson). Data was analyzed using FlowJo software (Tree Star).

(Expansion of Vγ9Vδ2 T Cells)

The Vγ9Vδ2 T cells used for expansion were prepared by isolating $CD3^+$ and $Vγ9^+$ cells from PBMCs in peripheral blood using FACSAria. Cell culture was performed (2 mL/well) in a 24-well plate (Nunc) containing a complete culture medium supplemented with 20 IU/mL of IL-2 (NOVARTIS). $1×10^6$ Vγ9Vδ2 T cells and $5×10^5$ irradiated (100 Gy) K80/4-1BBL/CD83, K80/4-1BBL or K80/CD83 cells were added to each well. And then, the cells were incubated at 37° C. under a 5% $CO_2$ condition.

The growing Vγ9Vδ2 T cells were harvested every 3 or 4 days, counted, and stimulated again at 7 to 10-day intervals. The Vγ9Vδ2 T cells were plated again at $1 × 10^6$ cells/well in addition to $5 × 10^5$ irradiated artificial APCs, and loaded in a complete culture medium under conditions of 37° C. and 5% $CO_2$.

PBMCs were stimulated with 5 μM zoledronic acid (Novartis) in a complete culture medium consisting of 1640 RPMI (Lonza) containing 10% inactivated FBS. An IL-2 (1000 IU/mL)-containing medium was added every 3 or 4 days, and the culture were transferred to a new 24-well plate under conditions of 37° C. and 5% $CO_2$.

The Vγ9Vδ2 T cells were centrifuged with a Ficoll-Paque density gradient to remove dead Vγ9Vδ2 T cells and remaining artificial APCs, and then cryopreserved in liquid nitrogen until further use.

(ELISA)

Vγ9Vδ2 T cells were stimulated with K80/4-1BBL/CD83, K80/4-1BBL or K80/83, and 20 IU/mL of IL-2-loaded artificial APCs in a complete medium at 37° C. for 72 hours. A supernatant was collected, centrifuged to remove cell debris, and then stored at −20° C. The concentrations of IL-2, IL-6, IFN-γ, TNF-α, GM-CSF, IL-4, IL-10, TGF-β, and IL-17a in the supernatant were measured through ELISA (BioLegend) according to the manufacturer's instructions.

(Analysis of RNA Expression By Reverse Transcription-PCR)

Vγ9Vδ2 T cells were stimulated with K80/4-1BBL/CD83, K80/4-1BBL or K80/83 and 20 IU/mL of IL-2-loaded artificial APCs in a complete medium at 37° C. for 7 days. The Vγ9Vδ2 T cells were harvested, and total RNA was extracted using an RNeasy Mini kit (QIAGEN). In a reverse transcription reaction, cDNA was synthesized using a Transcriptor First Strand cDNA Synthesis kit (Roche) with a 2.5 μM anchored-oligo (dT) primer and Transcriptor Reverse Transcriptase (Roche), and amplified by PCR using the following primers:

GAPDH forward, (SEQ ID NO: 5)
5'-TGTTGCCATCAATGACCCCTT-3',

GAPDH reverse, (SEQ ID NO: 6)
5'-CTCCACGACGTACTCAGCG-3';

perforin forward, (SEQ ID NO: 7)
5'-GGCTGGACGTGACTCCTAAG-3', perforin reverse, (SEQ ID NO: 8)
5'-CTGGGTGGAGGCGTTGAAG-3';

granzyme A forward, (SEQ ID NO: 9)
5'-GTGCTGGGGCTTTGATTGC-3', granzyme A reverse: (SEQ ID NO: 10)
5'-GGGTCATAGCATGGATAGGGAAA-3';

granzyme B forward, (SEQ ID NO: 11)
5'-TGGGGGACCCAGAGATTAAAA-3', granzyme B reverse, (SEQ ID NO: 12)
5'-TTTCGTCCATAGGAGACAATGC-3';

FasL forward, (SEQ ID NO: 13)
5'-GAACTCCGAGAGTCT ACCAGC-3',

FasL reverse, (SEQ ID NO: 14)
5'-TTGCCTGTTAAATGGGCCACT-3';

TNF-α forward, (SEQ ID NO: 15)
5'-ATGAGCACTGAAAGCATGATCC-3',

TNF-α reverse, (SEQ ID NO: 16)
5'-GAGGGCTGATTAGAGAGAGGTC-3';

IFN-γ forward, (SEQ ID NO: 17)
5'-CTCTTGGCTGTTACTGCCAGG-3',

IFN-γ reverse, (SEQ ID NO: 18)
5'-CTCCACACTCTTTTGGATGCT-3';

BCL2 forward, (SEQ ID NO: 19)
5'-GGTGGGGTCATGTGTGTGG-3',

BCL2 reverse, (SEQ ID NO: 20)
5'-CGGTTCAGGTACTCAGTCATCC-3';

BCL2A 1 forward, (SEQ ID NO: 21)
5'-TTACAGGCTGGCTCAGGACT-3',

BCL2A 1 reverse, (SEQ ID NO: 22)
5'-CCCAGTTAATGATGCCGTCT-3';

Bcl-xL forward, (SEQ ID NO: 23)
5'-AGCCTTGGATCCAGGAGAAC-3',

Bcl-xL reverse, (SEQ ID NO: 24)
5'-AGCGGTTGAAGCGTTCCT-3'

All of the above primers were disclosed previously (De-Barros, A. et al. *Eur J Immunol* 2011. 41: 195-201; Dokouhaki, P. et al. *Cancer Lett* 2010. 297: 126-136).

For each specimen, 20 μL of a reaction mixture contained a reaction buffer, 1 mM of each deoxynucleotide mixture, 20U of Protector RNase Inhibitor, 10 pM of each primer, 10U of Transcriptor Reverse Transcriptase. The thermocycling program was as follows: 50° C. for 1 hour and 83° C. for 10 minutes for cDNA amplification. The housekeeping gene GAPDH was used as a reference gene for quantification. The product was isolated from a 1.2% agarose gel at 100 volts for 25 minutes. mRNA was analyzed using Image Lab software (BIO-RAD).

(Cytotoxicity Assay)

A standard $^{51}$Cr-release assay was performed, as described in Park, M. Y. et al. *Eur J Immunol* 2008. 38: 2106-2117. Simply put, K562 and Daudi cell lines were incubated with 100 mCi [$^{51}$Cr] sodium chromate/1×10$^6$ cells under conditions of 37° C. and 5% $CO_2$ for 1 hour. The $^{51}$Cr-labeled target cells were incubated with effector cells, i.e., Vγ9Vδ2 T cells, at 37° C. for 4 hours. The supernatant (100 μL) was harvested, and radioactivity was counted using a gamma counter (Packard). The percent specific incorporation was calculated by the formula: [(experimental release-spontaneous release)/(maximum release-spontaneous release)]×100. The spontaneous release and the maximum release were measured in media and in the presence of 2% Triton-X100.

(Statistical Analysis)

All data was analyzed using a statistic program GraphPad Prism 5.0 (GraphPad Software Inc.). The difference between values was evaluated using a Student's t-test. Significance was determined when $p<0.05$.

Experimental Example 1

Proliferation of γδ T Cells Using Feeder Cells

FIG. 1 is a diagram illustrating the proliferation of human γδ T cells in vitro by establishing stimulatory cells expressing costimulatory molecules CD83/4-1BBL/CD80, which are an immunostimulatory ligand-free K562 cell line, for the in vitro proliferation of γδ T cells.

Figure 2:
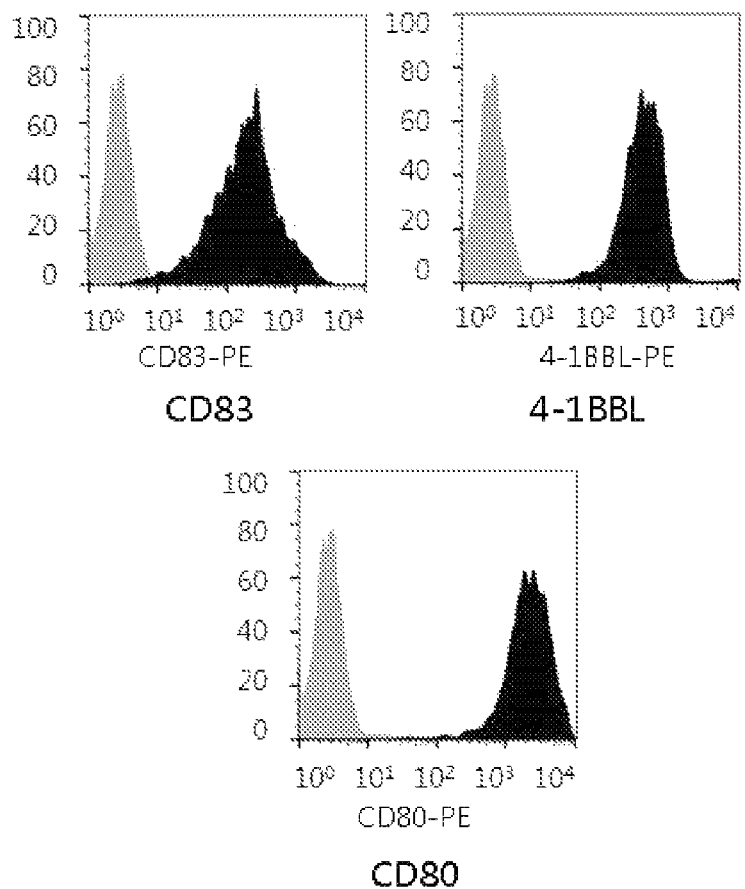
FIG. 2 shows the results of confirming the expression of costimulatory molecules 4-1BBL, CD80 and CD83, expressed in feeder cells, according to the present invention.

As shown in FIG. 2, the expression of costimulatory molecules CD83, 4-1BBL and CD80 in feeder cells established in a K562 cell line was confirmed.

Figure 3:
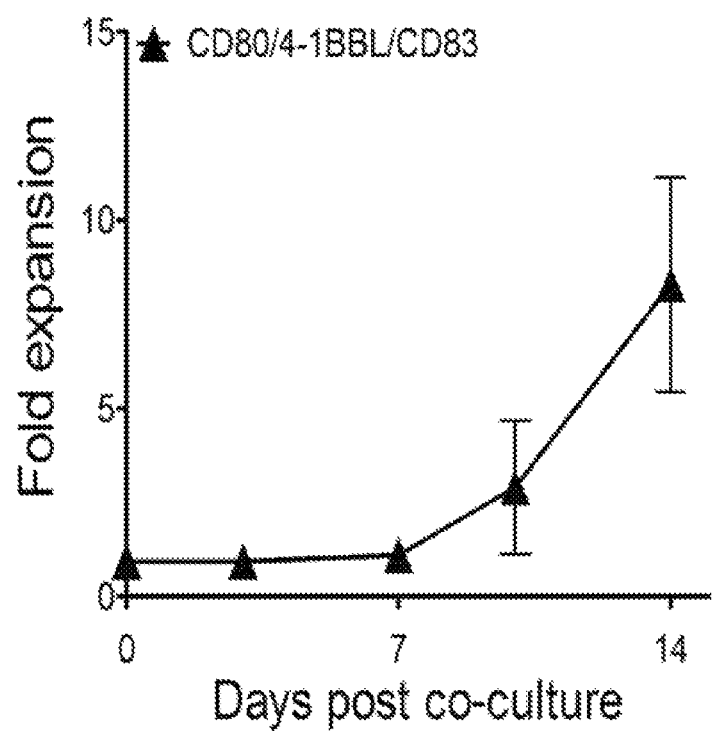
FIG. 3 shows the result of the proliferation of γδ T cells using feeder cells expressing 4-1BBL/CD80/CD83 according to the present invention.

FIG. 3 shows the result of in vitro proliferation of γδ T cells stimulated with feeder cells, demonstrating the proliferation of γδ T cells until 14 days after co-culture.

Figure 4:
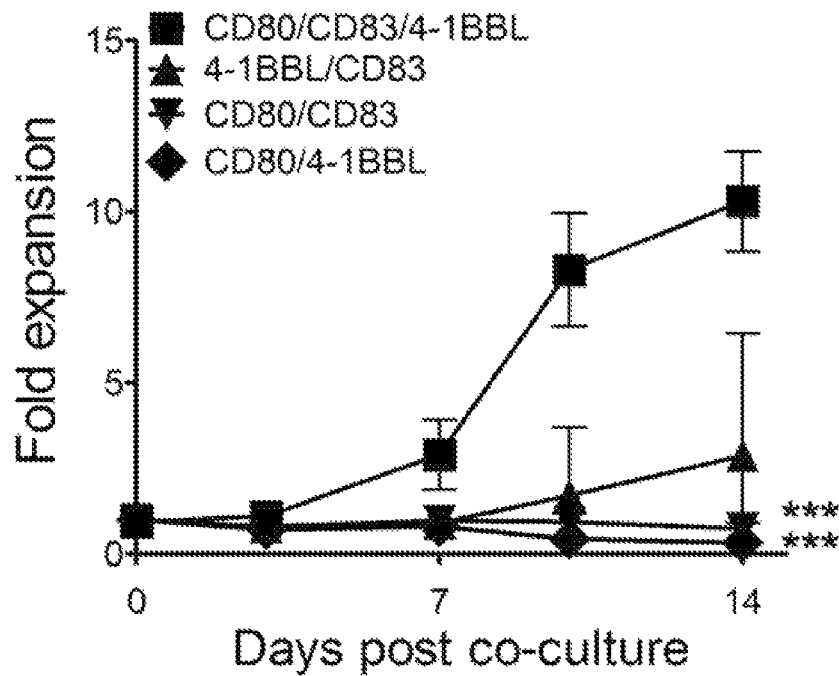
FIG. 4 shows the result of the proliferation of γδ T cells using feeder cells expressing a combination of different types of costimulatory molecules.

FIG. 4 shows the result of proliferating γδ T cells stimulated by feeder cells expressing a combination of different types of costimulatory molecules, demonstrating that the proliferation rate of γδ T cells when being stimulated with feeder cells expressing CD83, 4-1BBL and CD80 is the highest.

Experimental Example 2

Experiments for Proliferation and Differentiation Marker of γδ T Cells Using Feeder Cells 7 Days After Stimulation with Zoledronic Acid and IL-2

Figure 5A:
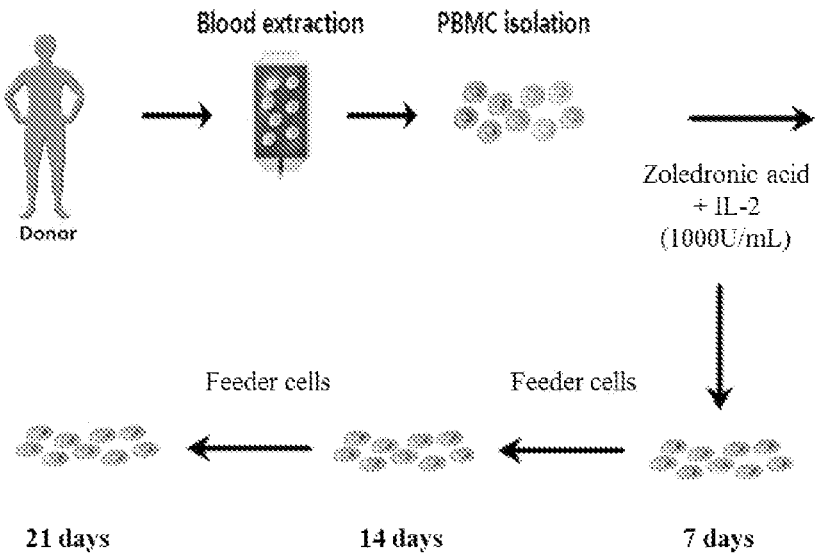
FIG. 5A is a diagram illustrating the process of stimulating feeder cells from human PBMCs in the presence of zoledronic acid and IL-2.

According to the stimulation process diagram shown in FIG. 5A, after the number of γδ T cells was increased by treating four types of human peripheral blood with zoledronic acid and IL-2 (1000 IU/mL) for 7 days, 7 days later, γδ T cells were stimulated using feeder cells and a low concentration of IL-2 (20 IU/mL) for 3 weeks without a separate purification process, for example, using microspheres or by FACS sorting.

Figure 5B:
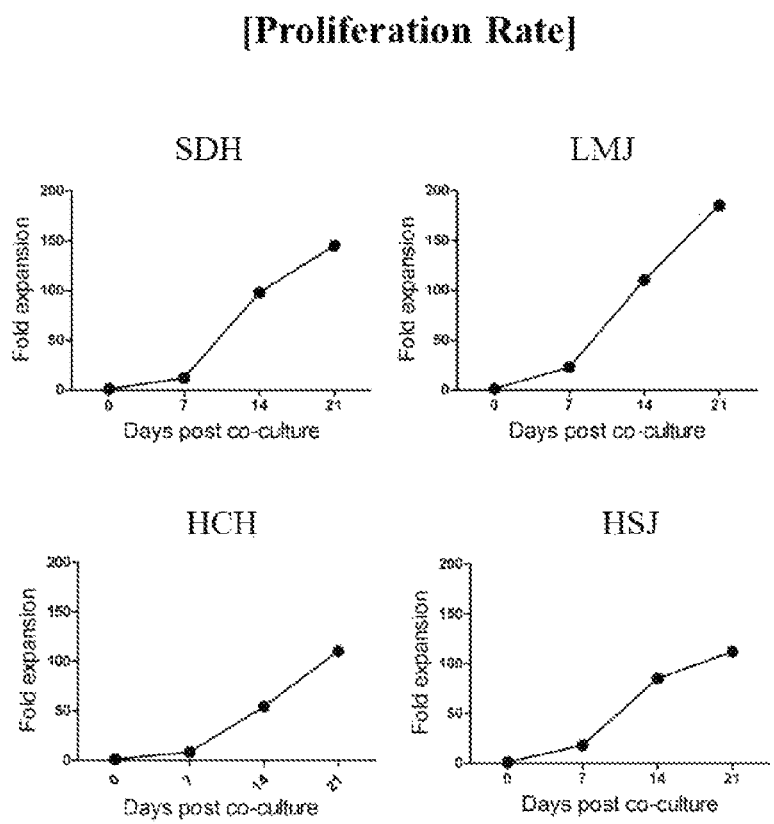
FIG. 5B is a graph showing the proliferation rate of γδ T cells obtained by stimulating enriched γδ T cells obtained by stimulating human PBMCs with zoledronic acid and IL-2 (1000 IU/mL) with feeder cells expressing 4-1BBL/CD80/CD83 in the presence of a low concentration of IL-2 (20 IU/mL).
Figure 6:
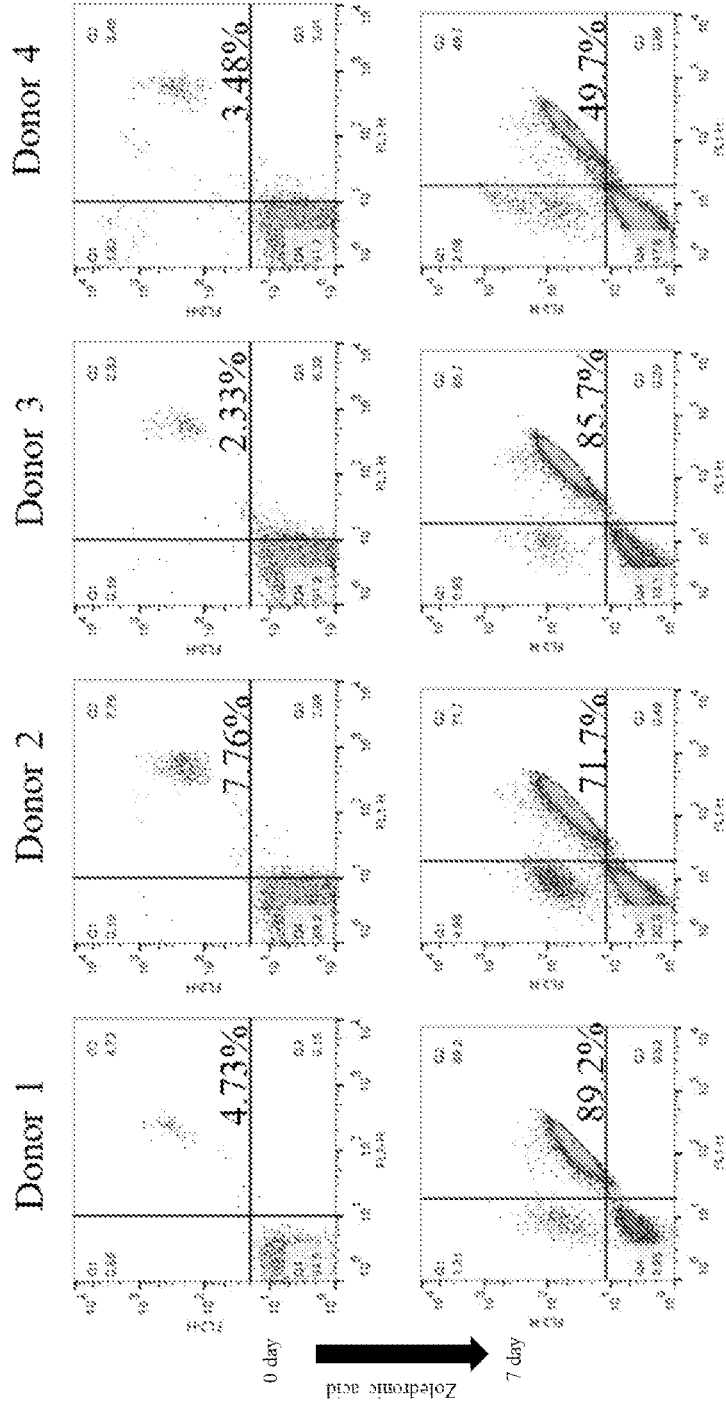
FIG. 6 is the FACS analysis result showing the proliferation rate of γδ T cells obtained by stimulating enriched γδ T cells obtained by stimulating human PBMCs with zoledronic acid and IL-2 (1000 IU/mL) with feeder cells expressing 4-1BBL/CD80/CD83 in the presence of a low concentration of IL-2 (20 IU/mL).

As shown in FIGS. 5B and 6, it was shown that the proliferation of γδ T cells was insignificant during 7 days of the treatment of four types of human peripheral blood with zoledronic acid and a high concentration of IL-2, but was rapidly increased during three weeks of the stimulation with stimulatory cells and a low concentration of IL-2.

Figure 7:
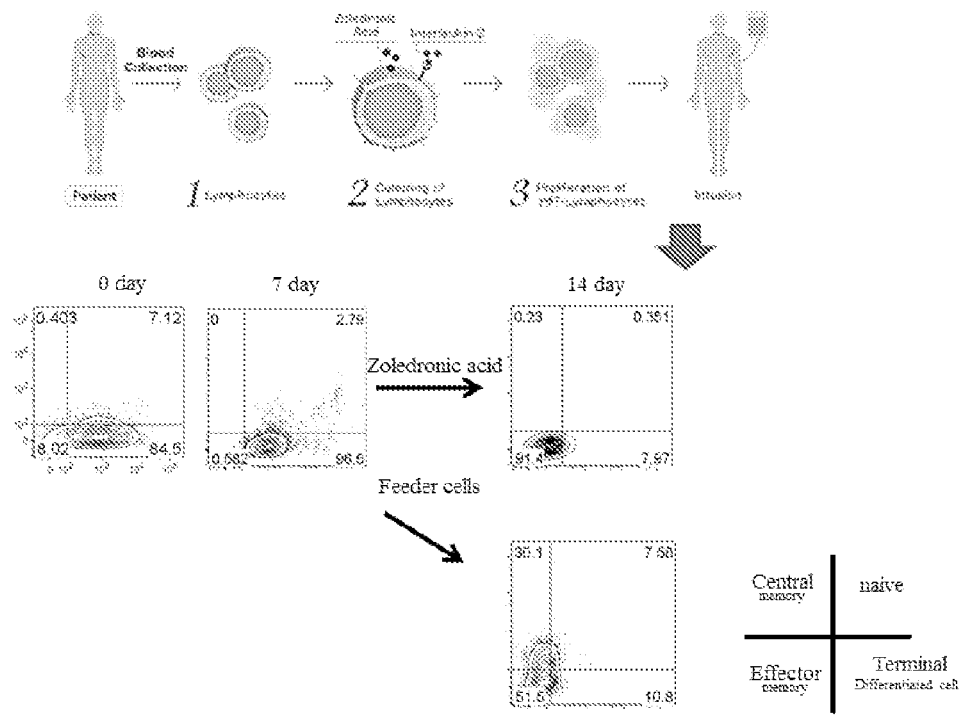
FIG. 7 is the FACS analysis (subsets analysis) result of a differentiation marker for γδ T cells obtained by stimulating enriched γδ T cells obtained by stimulating human PBMCs with zoledronic acid and IL-2 (1000 IU/mL) with feeder cells expressing 4-1BBL/CD80/CD83 in the presence of a low concentration of IL-2 (20 IU/mL).

In addition, most of the differentiation markers were identified as effector memory types in 7-day in vitro proliferation after the treatment of four types of human peripheral blood with zoledronic acid and a high concentration of IL-2 for 7 days (FIG. 7).

However, after the treatment with zoledronic acid and a high concentration of IL-2 for 7 days, γδ T cells were stimulated using feeder cells and a low concentration of IL-2 (20 IU/mL), and as a result of subsets analysis the γδ T cells, it was confirmed that, unlike γδ T cells stimulated only with zoledronic acid, there was subsets of central memory cells (FIG. 7).

Experimental Example 3

Experiment for Proliferation of γδ T Cells Using T Cell Receptor Stimulation

Figure 8A:
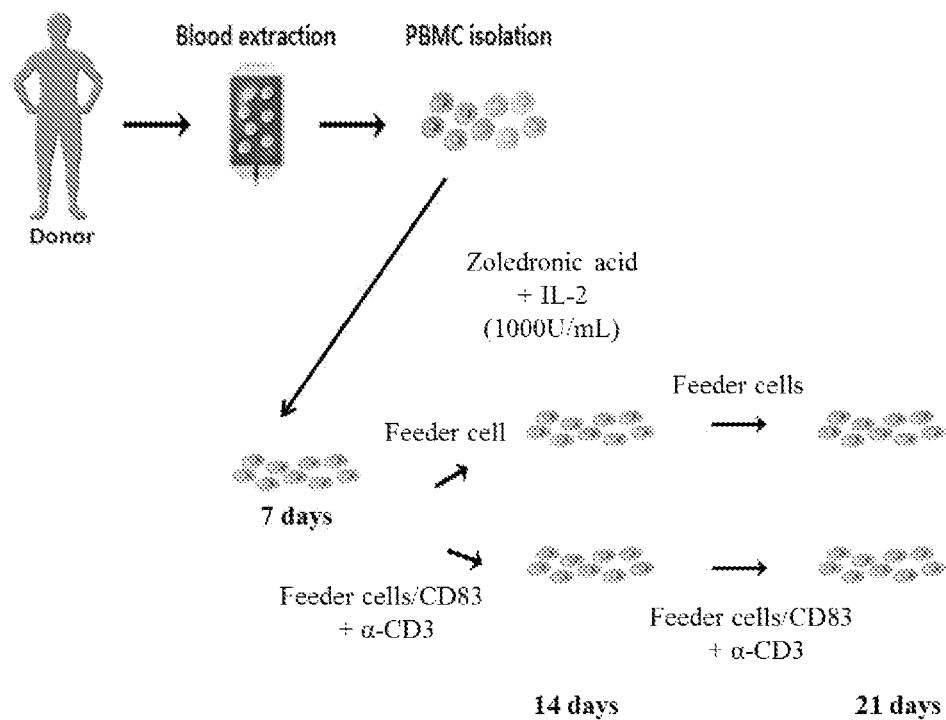
FIG. 8A is the diagram of the comparison with T cell receptor stimulation.

After the number of γδ T cells was increased through the treatment with zoledronic acid and IL-2 (1000 IU/mL) for 7 days, 7 days later, the γδ T cells were stimulated using feeder cells and a low concentration of IL-2 (20 IU/mL) without a separate purification process, for example, by using microspheres or through FACS sorting, and then subsets analysis was performed for the γδ T cells proliferated in vitro according to the presence or absence of an immunostimulatory ligand, which is an anti-CD3 antibody (refer to FIG. 8A).

Figure 8B:
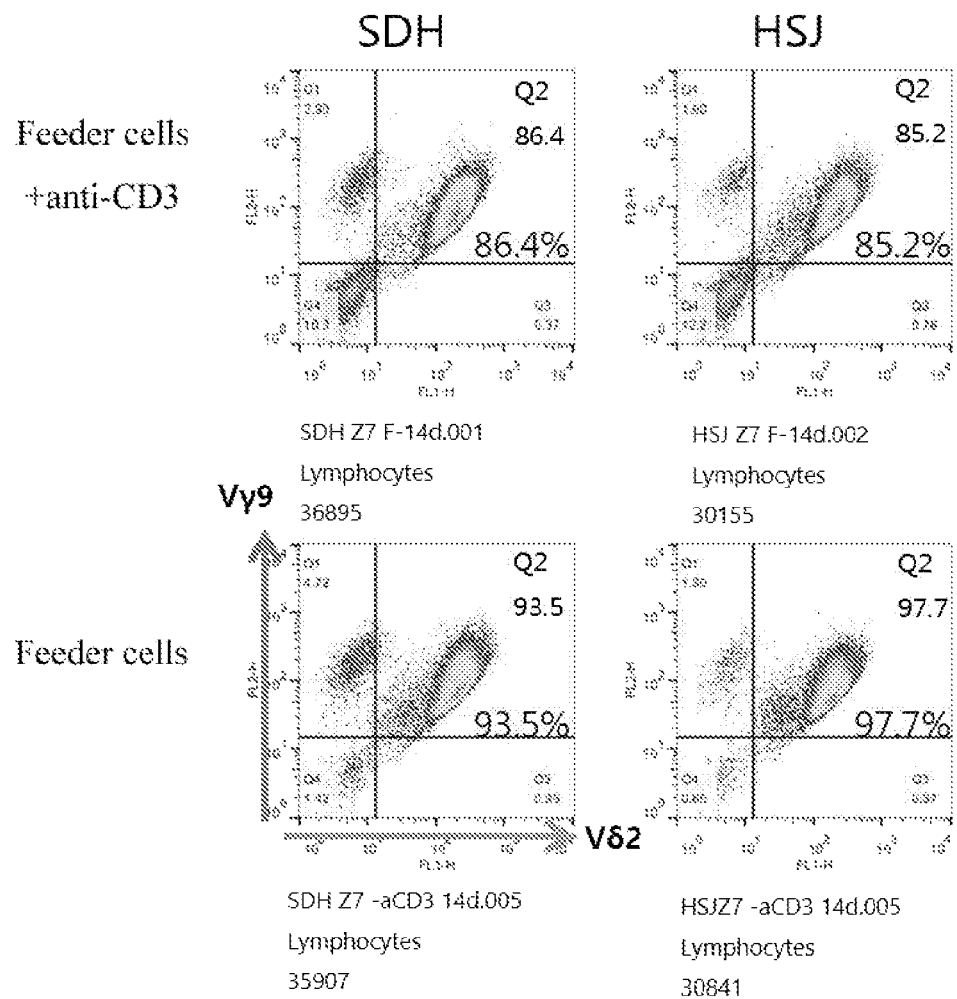
FIG. 8B is the FACS analysis (subsets analysis) result of γδ T cells proliferated in vitro by stimulating enriched γδ T cells obtained by stimulating human PBMCs with zoledronic acid and IL-2 (1000 IU/mL) with feeder cells expressing 4-1BBL/CD80/CD83 in the presence of a low concentration of IL-2 (20 IU/mL) according to the absence or presence of an anti-CD3 antibody.

As shown in FIG. 8B, it was confirmed that, when the anti-CD3 antibody was not used, the purity of Vγ9+/Vδ2+ T cells was higher.

As described above, it was found that the in vitro proliferation of γδ T cells using the stimulation of feeder cells expressing the costimulatory molecules such as CD80, CD83 and 4-1BBL is performed for a long time, differentiation into central memory cells, rather than γδ T cells induced by a phosphoantigen, lasts longer, and high purity γδ T cells were able to be obtained.

Experimental Example 4

Effect of Proliferating γδ T Cells Using Feeder Cells Expressing Various Costimulatory Molecules Among feeder cells expressing various types of costimulatory molecules, γδ T cells proliferated using feeder cells expressing all of 4-1BBL/CD80/CD83 exhibited the highest proliferation rate, the reason of which was proved by confirming the expression of an apoptosis-inhibiting molecule.

Figure 9:
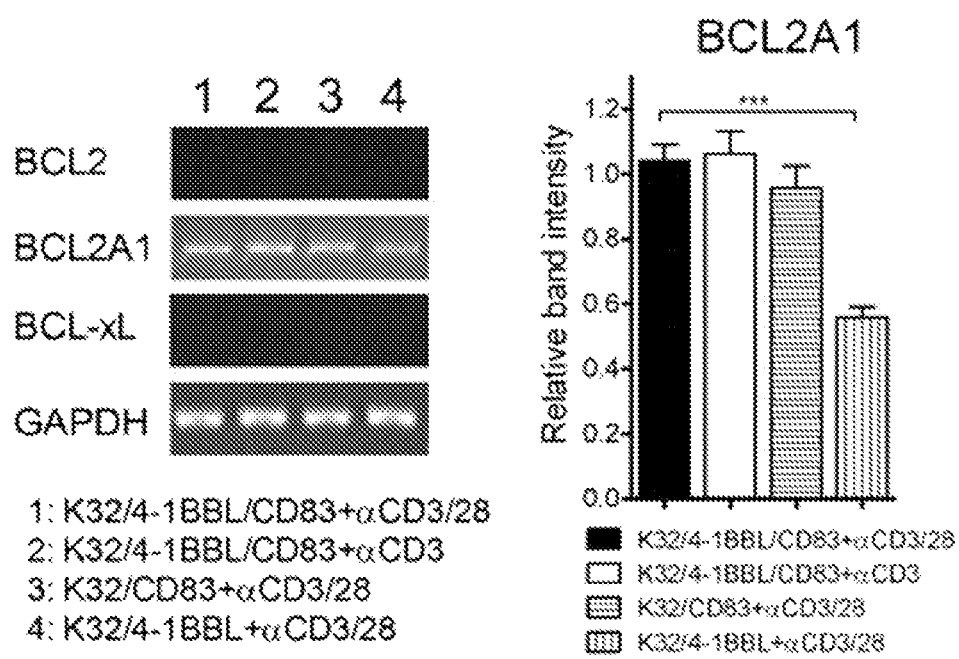
FIG. 9 is the RT-PCR result showing that anti-apoptotic molecule BCLA2A1 is expressed in γδ T cells proliferated using feeder cells expressing 4-1BBL/CD80/CD83.

FIG. 9 is that the RT-PCR result showing that anti-apoptotic molecule BCLA2A1 is expressed in γδ T cells proliferated using feeder cells expressing all of 4-1BBL/CD80/CD83.

Figure 10:
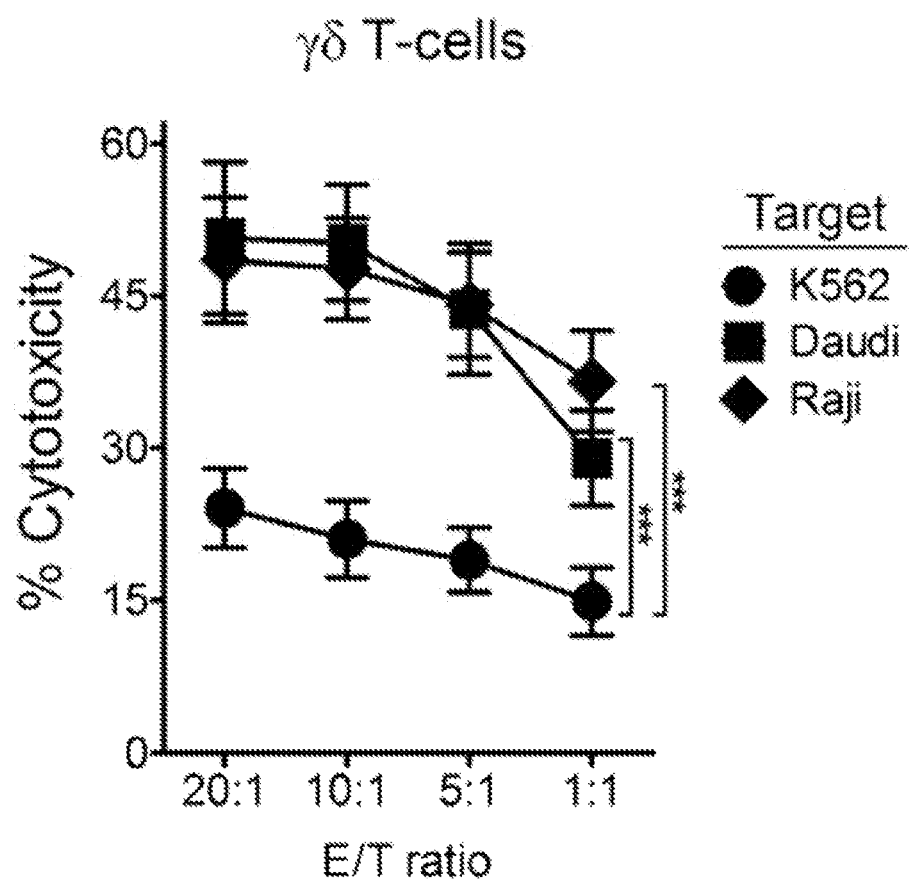
FIG. 10 is the result of confirming the cytotoxicity of γδ T cells proliferated using feeder cells expressing 4-1BBL/CD80/CD83 against tumor cells.

FIG. 10 is the result of confirming the cytotoxicity of γδ T cells proliferated using feeder cells expressing all of 4-1BBL/CD80/CD83 in Daudi and Raji tumor cell lines, confirming that the γδ T cells proliferated using feeder cells expressing all of 4-1BBL/CD80/CD83 will be used as cells killing allogenic tumor cells.

Experimental Example 5

Figure 11A:
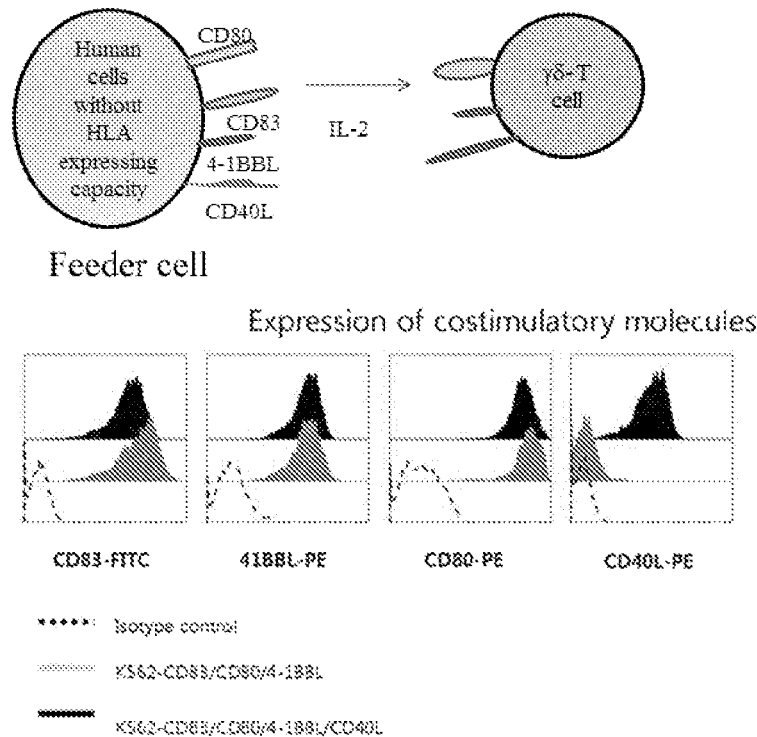
FIG. 11A is the FACS analysis result showing the expression of each costimulatory molecule in feeder cells expressing costimulatory molecules 4-1BBL/CD80/CD83/CD40L.

Experiment for Proliferation and Differentiation Marker of γδ T Cells Using Feeder Cells Expressing 4-1BBL/CD80/CD83/CD40L For in vitro proliferation of γδ T cells, feeder cells expressing costimulatory molecules 4-1BBL/CD80/CD83/CD40L, which are an immunostimulatory ligand-free K562 cell line, were established (FIG. 11A). After the number of γδ T cells was increased through the treatment of one type of human peripheral blood with zoledronic acid and IL-2 (1000 IU/mL) for 7 days, 7 days later, the γδ T cells were stimulated for 4 weeks using feeder cells and a low concentration of IL-2 (20 IU/mL) without a separate purification process, for example, by using microspheres or by FACS sorting. In addition to a proliferation rate, the purity and subsets analysis of the γδ T cells at day 14 and day 28 of the proliferation were analyzed.

Figure 11B:
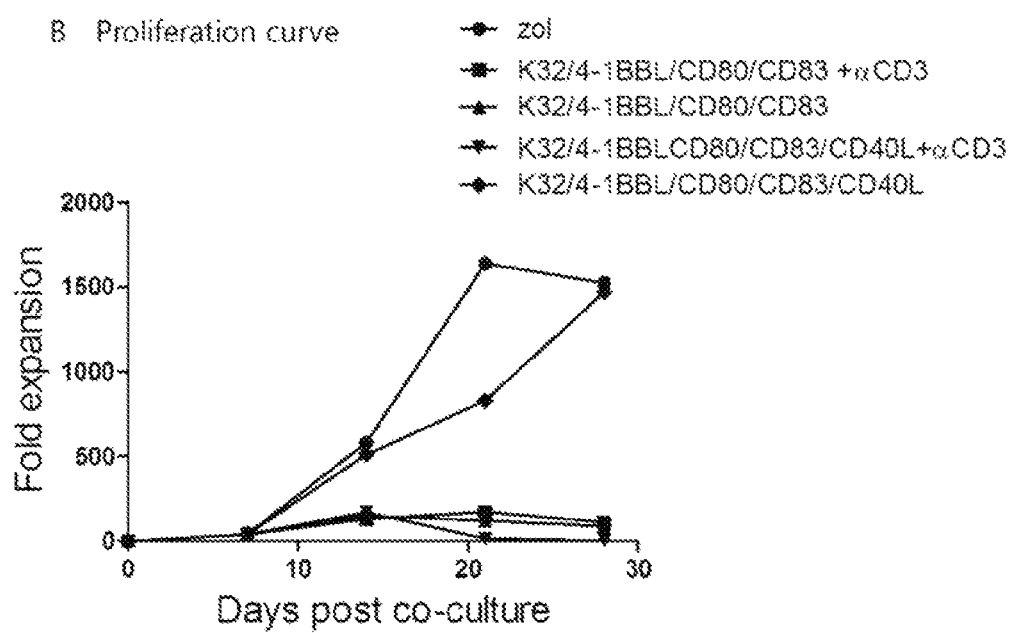
FIG. 11B is the result of proliferating γδ T cells in the absence or presence of an anti-CD3-antibody in the stimulation with feeder cells expressing 4-1BBL/CD80/CD83 and feeder cells expressing 4-1BBL/CD80/CD83/CD40L.

FIG. 11B shows the result of proliferation using zoledronic acid and a high concentration of IL-2 (1000 IU/mL) in the same human peripheral blood, the result of proliferation using feeder cells expressing 4-1BBL/CD80/CD83, and the result of in vitro proliferation of γδ T cells stimulated by feeder cells expressing 4-1BBL/CD80/CD83/CD40L until day 28.

Unlike the case using zoledronic acid, when the feeder cells expressing 4-1BBL/CD80/CD83/CD40L were used, it can be seen that, the cells were continuously proliferated over 21 days without a decrease in proliferation rate, and the proliferation rate was about 16.5 fold higher than when feeder cells expressing 4-1BBL/CD80/CD83 were used.

In addition, in the case of the feeder cells expressing 4-1BBL/CD80/CD83/CD40L, the γδ T cells were able to be proliferated when a T cell receptor was not stimulated with anti-CD3.

Figure 12:
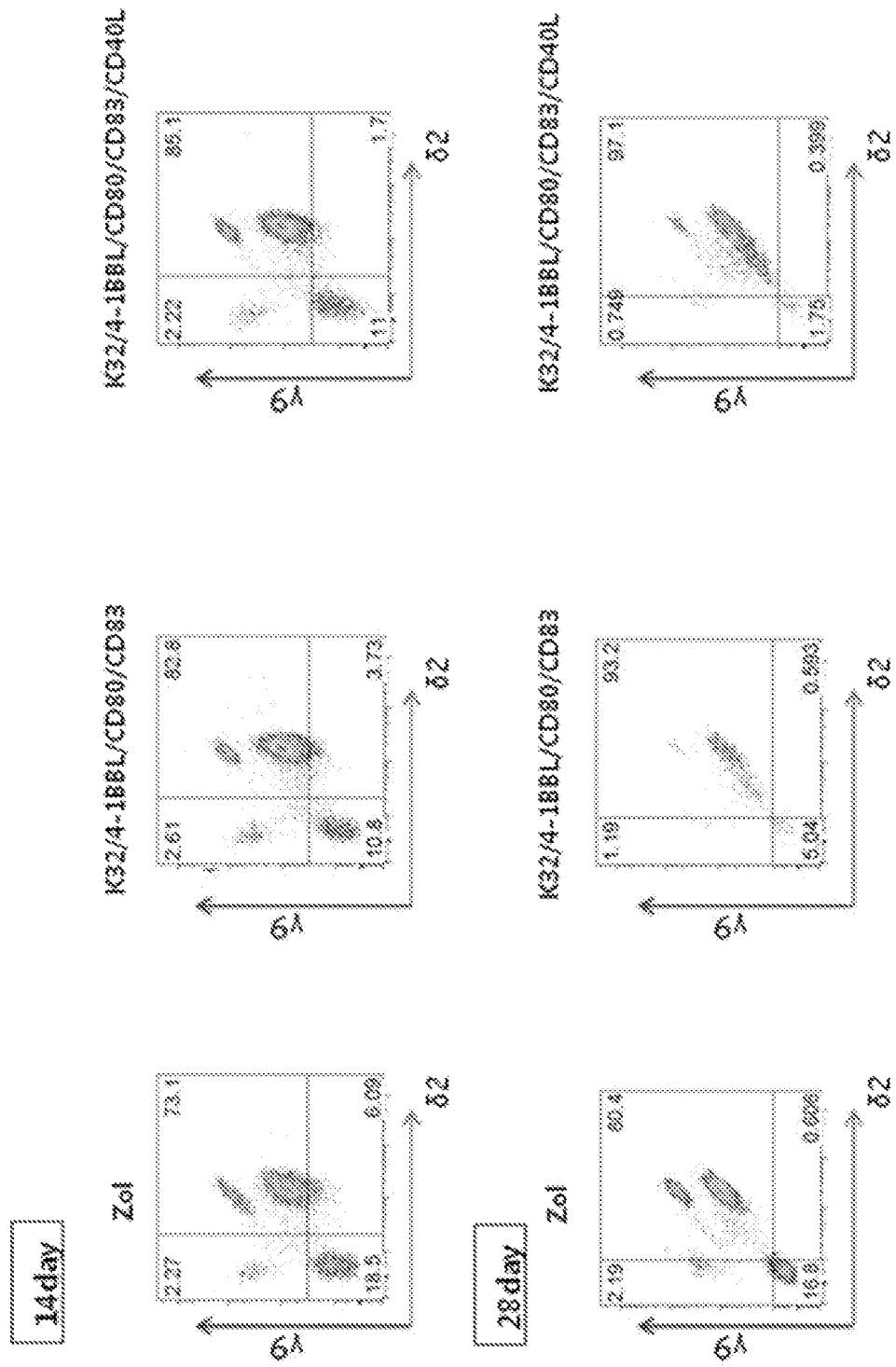
FIG. 12 is the result of the analysis of the purity of γδ T cells at day 14 and day 28 of the proliferation by the stimulation with feeder cells expressing 4-1BBL/CD80/CD83 and feeder cells expressing 4-1BBL/CD80/CD83/CD40L.

FIG. 12 shows the result of analyzing the purity of γδ T cells at day 14 and day 28 of proliferation, confirming that, when zoledronic acid and a high concentration of IL-2 (1000 IU/mL) were used, or when feeder cells expressing 4-1BBL/CD80/CD83/CD40L, rather than feeder cells expressing 4-1BBL/CD80/CD83, were used, the purity of Vγ9+/Vδ2+ T cells was higher.

Figure 13:
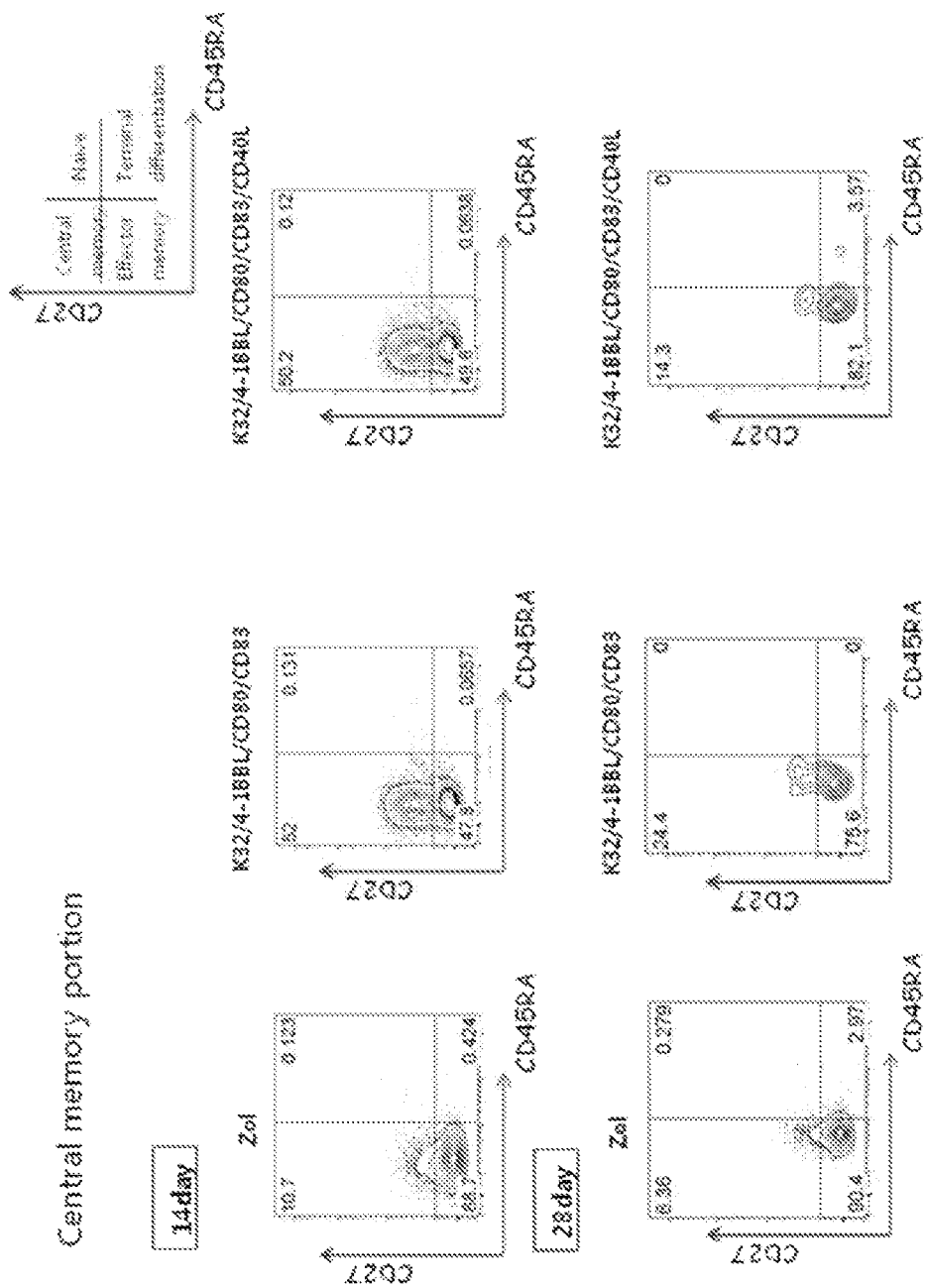
FIG. 13 is the result of analyzing the differentiation ability of γδ T cells into central memory cells at day 14 and day 28 of the proliferation by the stimulation with feeder cells expressing 4-1BBL/CD80/CD83 and feeder cells expressing 4-1BBL/CD80/CD83/CD40L.

FIG. 13 shows the result of subsets analysis γδ T cells at day 14 and day of proliferation, confirming that the feeder cells expressing 4-1BBL/CD80/CD83/CD40L exhibited lower differentiation into central memory cells and maintenance than the case using the feeder cells expressing 4-1BBL/CD80/CD83, but higher differentiation into central memory cells and maintenance than the case using zoledronic acid and a high concentration of IL-2 (1000 IU/mL).

As described above, it was found that the in vitro proliferation of γδ T cells using the stimulation with the feeder cells expressing 4-1BBL/CD80/CD83/CD40L was able to be performed for a long time, and obtained higher purity γδ T cells than those induced by a phosphoantigen or the stimulation with the feeder cells expressing 4-1BBL/CD80/CD83, and compared to the γδ T cells induced by phosphoantigen stimulation, the differentiation of the γδ T cells proliferated using the feeder cells expressing 4-1BBL/CD80/CD83/CD40L into central memory cells is longer maintained.

The present invention may be applied to the field of adoptive immunotherapy.

What is claimed is:

1. A method of in vitro proliferating, γδ T cells, comprising:
stimulating isolated human PBMCs comprising γδ T cells with zoledronic acid and IL-2 for a first period to generate enriched γδ T cells, and then stimulating enriched γδ T cells in the isolated human PBMCs by co-culture with human leukocyte antigen (HLA) deficient feeder cells expressing 4-1BBL, CD80, CD83 and CD40L in the presence of IL-2 and without an anti-CD3 antibody for a second period to obtain proliferating γδ T cells,
wherein the feeder cells are prepared by transducing nucleic acids encoding a costimulatory molecule group consisting of 4-1BBL, CD80, CD83 and CD40L, into isolated K562 cells that do not express HLA.

2. The method according to claim 1, wherein the in vitro proliferation of the enriched γδ T cells is performed in the presence of 20 to 100 IU/mL of IL-2.

3. The method according to claim 1, wherein the co-culture is performed for 14 to 100 days.

* * * * *

SEQUENCE LISTING

```
<160> NUMBER OF SEQ ID NOS: 32

<210> SEQ ID NO 1
<211> LENGTH: 765
<212> TYPE: DNA
<213> ORGANISM: Homo sapiens

<400> SEQUENCE: 1
atggaatacg cctctgacgc ttcactggac cccgaagccc cgtggcctcc cgcgccccgc      60
gctcgcgcct gccgcgtact gccttgggcc ctggtcgcgg ggctgctgct gctgctgctg     120
ctcgctgccg cctgcgccgt cttcctcgcc tgcccctggg ccgtgtccgg ggctcgcgcc     180
tcgcccggct ccgcggccag cccgagactc cgcgagggtc ccgagctttc gcccgacgat     240
cccgccggcc tcttggacct gcggcagggc atgtttgcgc agctggtggc ccaaaatgtt     300
ctgctgatcg atgggcccct gagctggtac agtgacccag gcctggcagg cgtgtccctg     360 acgggggggcc tgagctacaa agaggacacg aaggagctgg tggtggccaa ggctggagtc     420
tactatgtct tctttcaact agagctgcgg cgcgtggtgg ccggcgaggg ctcaggctcc     480
gtttcacttg cgctgcacct gcagccactg cgctctgctg ctggggccgc cgccctggct     540
ttgaccgtgg acctgccacc cgcctcctcc gaggctcgga actcggcctt cggtttccag     600
ggccgcttgc tgcacctgag tgccggccag cgcctgggcg tccatcttca cactgaggcc     660
agggcacgcc atgcctggca gcttaccag ggcgccacag tcttgggact cttccgggtg     720 accccgaaa tcccagccgg actcccttca ccgaggtcgg aataa                      765
```

<210> SEQ ID NO 2
<211> LENGTH: 1734
<212> TYPE: DNA
<213> ORGANISM: Homo sapiens

<400> SEQUENCE: 2

| | |
|---|---|
| atgggccaca cacggaggca gggaacatca ccatccaagt gtccatacct caatttcttt | 60 |
| cagctcttgg tgctggctgg tctttctcac ttctgttcag gtgttatcca cgtgaccaag | 120 |
| gaagtgaaag aagtggcaac gctgtcctgt ggtcacaatg tttctgttga agagctggca | 180 |
| caaactcgca tctactggca aaaggagaag aaaatggtgc tgactatgat gtctggggac | 240 |
| atgaatatat ggcccgagta caagaaccgg accatctttg atatcactaa taacctctcc | 300 |
| attgtgatcc tggctctgcg cccatctgac gagggcacat acgagtgtgt tgttctgaag | 360 |
| tatgaaaaag acgctttcaa gcgggaacac ctggctgaag tgacgttatc agtcaaagct | 420 |
| gacttcccta cacctagtat atctgacttt gaaattccaa cttctaatat tagaaggata | 480 |
| atttgctcaa cctctggagg ttttccagag cctcacctct cctggttgga aaatggagaa | 540 |
| gaattaaatg ccatcaacac aacagtttcc caagatcctg aaactgagct ctatgctgtt | 600 |
| agcagcaaac tggatttcaa tatgacaacc aaccacagct tcatgtgtct catcaagtat | 660 |
| ggacatttaa gagtgaatca gaccttcaac tggaatacaa ccaagcaaga gcatttttcct | 720 |
| gataacctgc tcccatcctg gccattacc ttaatctcag taaatggaat ttttgtgata | 780 |
| tgctgcctga cctactgctt tgccccaaga tgcagagaga aaggaggaa tgagagattg | 840 |
| agaagggaaa gtgtacgccc tgtataaatg gccacacac ggaggcaggg aacatcacca | 900 |
| tccaagtgtc catacctcaa tttctttcag ctcttggtgc tggctggtct ttctcacttc | 960 |
| tgttcaggtg ttatccacgt gaccaaggaa gtgaaagaag tggcaacgct gtcctgtggt | 1020 |
| cacaatgttt ctgttgaaga gctggcacaa actcgcatct actggcaaaa ggagaagaaa | 1080 |
| atggtgctga ctatgatgtc tggggacatg aatatatggc ccgagtacaa gaaccggacc | 1140 |
| atctttgata tcactaataa cctctccatt gtgatcctgg ctctgcgccc atctgacgag | 1200 |
| ggcacatacg agtgtgttgt tctgaagtat gaaaaagacg ctttcaagcg ggaacacctg | 1260 |
| gctgaagtga cgttatcagt caaagctgac ttccctacac ctagtatatc tgactttgaa | 1320 |
| attccaactt ctaatattag aaggataatt tgctcaacct ctggaggttt tccagagcct | 1380 |
| cacctctcct ggttggaaaa tggagaagaa ttaaatgcca tcaacacaac agtttcccaa | 1440 |
| gatcctgaaa ctgagctcta tgctgttagc agcaaactgg atttcaatat gacaaccaac | 1500 |
| cacagcttca tgtgtctcat caagtatgga catttaagag tgaatcagac cttcaactgg | 1560 |
| aatacaacca agcaagagca ttttcctgat aacctgctcc catcctgggc cattacctta | 1620 |
| atctcagtaa atggaatttt tgtgatatgc tgcctgacct actgctttgc cccaagatgc | 1680 |
| agagagagaa ggaggaatga gagattgaga agggaaagtg tacgccctgt ataa | 1734 |

<210> SEQ ID NO 3
<211> LENGTH: 618
<212> TYPE: DNA
<213> ORGANISM: Homo sapiens

<400> SEQUENCE: 3

| | |
|---|---|
| atgtcgcgcg gcctccagct tctgctcctg agctgcgcct acagcctggc tcccgcgacg | 60 |
| ccggaggtga aggtggcttg ctccgaagat gtggacttgc cctgcaccgc ccctgggat | 120 |
| ccgcaggttc cctacacggt ctcctgggtc aagttattgg agggtggtga agagaggatg | 180 |

```
gagacacccc aggaagacca cctcagggga cagcactatc atcagaaggg gcaaaatggt    240
tctttcgacg cccccaatga aaggccctat tccctgaaga tccgaaacac taccagctgc    300
aactcgggga catacaggtg cactctgcag gacccggatg ggcagagaaa cctaagtggc    360
aaggtgatct tgagagtgac aggatgccct gcacagcgta aagaagagac ttttaagaaa    420
tacagagcgg agattgtcct gctgctggct ctggttattt tctacttaac actcatcatt    480
ttcacttgta agtttgcacg gctacagagt atcttcccag attttctaa  agctggcatg    540 gaacgagctt ttctcccagt tacctcccca ataagcatt  tagggctagt gactcctcac    600
aagacagaac tggtatag                                                  618

<210> SEQ ID NO 4
<211> LENGTH: 786
<212> TYPE: DNA
<213> ORGANISM: Homo sapiens

<400> SEQUENCE: 4
atgatcgaaa catacaacca aacttctccc cgatctgcgg ccactggact gcccatcagc     60
atgaaaattt ttatgtattt acttactgtt tttcttatca cccagatgat tgggtcagca    120 cttttttgctg tgtatcttca tagaaggctg gacaagatag aagatgaaag gaatcttcat    180
gaagattttg tattcatgaa aacgatacag agatgcaaca caggagaaag atccttatcc    240
ttactgaact gtgaggagat taaaagccag tttgaaggct tgtgaagga tataatgtta    300 aacaaagagg agacgaagaa agaaaacagc tttgaaatgc aaaaaggtga tcagaatcct    360
caaattgcgg cacatgtcat aagtgaggcc agcagtaaaa caacatctgt gttacagtgg    420
gctgaaaaag gatactacac catgagcaac aacttggtaa ccctggaaaa tgggaaacag    480
ctgaccgtta aaagacaagg actctattat atctatgccc aagtcacctt ctgttccaat    540
cgggaagctt cgagtcaagc tccatttata gccagcctct gcctaaagtc ccccggtaga    600
ttcgagagaa tcttactcag agctgcaaat acccacagtt ccgccaaacc ttgcgggcaa    660
caatccattc acttgggagg agtatttgaa ttgcaaccag gtgcttcggt gtttgtcaat    720
gtgactgatc caagccaagt gagccatggc actggcttca cgtcctttgg cttactcaaa    780
ctctga                                                              786

<210> SEQ ID NO 5
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 5
tgttgccatc aatgacccct t                                              21

<210> SEQ ID NO 6
<211> LENGTH: 19
<212> TYPE: DNA
<213> ORGANISM: Artificial Sequence
<220> FEATURE:
<223> OTHER INFORMATION: GAPDH reverse primer

<400> SEQUENCE: 6
ctccacgacg tactcagcg                                                 19

<210> SEQ ID NO 7
```

```
<211> LENGTH: 20
<212> TYPE: DNA
<213> ORGANISM: Artificial Sequence
<220> FEATURE:
<223> OTHER INFORMATION: perforin forward primer

<400> SEQUENCE: 7
ggctggacgt gactcctaag                                              20

<210> SEQ ID NO 8
<211> LENGTH: 19
<212> TYPE: DNA
<213> ORGANISM: Artificial Sequence
<220> FEATURE:
<223> OTHER INFORMATION: perforin reverse primer

<400> SEQUENCE: 8
ctgggtggag gcgttgaag                                               19

<210> SEQ ID NO 9
<211> LENGTH: 19
<212> TYPE: DNA
<213> ORGANISM: Artificial Sequence
<220> FEATURE:
<223> OTHER INFORMATION: granzyme A forward primer

<400> SEQUENCE: 9
gtgctggggc tttgattgc                                               19

<210> SEQ ID NO 10
<211> LENGTH: 23
<212> TYPE: DNA
<213> ORGANISM: Artificial Sequence
<220> FEATURE:
<223> OTHER INFORMATION: granzyme A reverse primer

<400> SEQUENCE: 10
gggtcatagc atggataggg aaa                                          23

<210> SEQ ID NO 11
<211> LENGTH: 21
<212> TYPE: DNA
<213> ORGANISM: Artificial Sequence
<220> FEATURE:
<223> OTHER INFORMATION: granzyme B forward primer

<400> SEQUENCE: 11
tgggggaccc agagattaaa a                                            21

<210> SEQ ID NO 12
<211> LENGTH: 22
<212> TYPE: DNA
<213> ORGANISM: Artificial Sequence
<220> FEATURE:
<223> OTHER INFORMATION: granzyme B reverse primer

<400> SEQUENCE: 12
tttcgtccat aggagacaat gc                                           22

<210> SEQ ID NO 13
<211> LENGTH: 21
<212> TYPE: DNA
<213> ORGANISM: Artificial Sequence
<220> FEATURE:
<223> OTHER INFORMATION: FasL forward primer

<400> SEQUENCE: 13
```
gaactccgag agtctaccag c                                              21

<210> SEQ ID NO 14
<211> LENGTH: 21
<212> TYPE: DNA
<213> ORGANISM: Artificial Sequence
<220> FEATURE:
<223> OTHER INFORMATION: FasL reverse primer

<400> SEQUENCE: 14
ttgcctgtta aatgggccac t                                              21

<210> SEQ ID NO 15
<211> LENGTH: 22
<212> TYPE: DNA
<213> ORGANISM: Artificial Sequence
<220> FEATURE:
<223> OTHER INFORMATION: TNF alpha forward primer

<400> SEQUENCE: 15
atgagcactg aaagcatgat cc                                             22

<210> SEQ ID NO 16
<211> LENGTH: 22
<212> TYPE: DNA
<213> ORGANISM: Artificial Sequence
<220> FEATURE:
<223> OTHER INFORMATION: TNF alpha reverse primer

<400> SEQUENCE: 16
gagggctgat tagagagagg tc                                             22

<210> SEQ ID NO 17
<211> LENGTH: 21
<212> TYPE: DNA
<213> ORGANISM: Artificial Sequence
<220> FEATURE:
<223> OTHER INFORMATION: IFN gamma forward primer

<400> SEQUENCE: 17
ctcttggctg ttactgccag g                                              21

<210> SEQ ID NO 18
<211> LENGTH: 21
<212> TYPE: DNA
<213> ORGANISM: Artificial Sequence
<220> FEATURE:
<223> OTHER INFORMATION: IFN gamma reverse primer

<400> SEQUENCE: 18
ctccacactc ttttggatgc t                                              21

<210> SEQ ID NO 19
<211> LENGTH: 19
<212> TYPE: DNA
<213> ORGANISM: Artificial Sequence
<220> FEATURE:
<223> OTHER INFORMATION: BCL2 forward primer

<400> SEQUENCE: 19
ggtggggtca tgtgtgtgg                                                 19

<210> SEQ ID NO 20
<211> LENGTH: 22
<212> TYPE: DNA

```
<213> ORGANISM: Artificial Sequence
<220> FEATURE:
<223> OTHER INFORMATION: BCL2 reverse primer

<400> SEQUENCE: 20
cggttcaggt actcagtcat cc                                              22

<210> SEQ ID NO 21
<211> LENGTH: 20
<212> TYPE: DNA
<213> ORGANISM: Artificial Sequence
<220> FEATURE:
<223> OTHER INFORMATION: BCL2A 1 forward primer

<400> SEQUENCE: 21
ttacaggctg gctcaggact                                                 20

<210> SEQ ID NO 22
<211> LENGTH: 20
<212> TYPE: DNA
<213> ORGANISM: Artificial Sequence
<220> FEATURE:
<223> OTHER INFORMATION: BCL2A 1 reverse primer

<400> SEQUENCE: 22
cccagttaat gatgccgtct                                                 20

<210> SEQ ID NO 23
<211> LENGTH: 20
<212> TYPE: DNA
<213> ORGANISM: Artificial Sequence
<220> FEATURE:
<223> OTHER INFORMATION: Bcl-xL forward primer

<400> SEQUENCE: 23
agccttggat ccaggagaac                                                 20

<210> SEQ ID NO 24
<211> LENGTH: 18
<212> TYPE: DNA
<213> ORGANISM: Artificial Sequence
<220> FEATURE:
<223> OTHER INFORMATION: Bcl-xL reverse primer

<400> SEQUENCE: 24
agcggttgaa gcgttcct                                                   18

<210> SEQ ID NO 25
<211> LENGTH: 8
<212> TYPE: PRT
<213> ORGANISM: Artificial Sequence
<220> FEATURE:
<223> OTHER INFORMATION: Ova257 peptide

<400> SEQUENCE: 25

Ser Ile Ile Asn Phe Glu Lys Leu
1               5

<210> SEQ ID NO 26
<211> LENGTH: 9
<212> TYPE: PRT
<213> ORGANISM: Artificial Sequence
<220> FEATURE:
<223> OTHER INFORMATION: tyrosinase-related protein 1 455 (Trp1455)

<400> SEQUENCE: 26
```

```
Thr Ala Pro Asp Asn Leu Gly Tyr Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Trp2180 peptide

<400> SEQUENCE: 27

Ser Val Tyr Asp Phe Phe Val Trp Leu
1               5

<210> SEQ ID NO 28
<211> LENGTH: 9
<212> TYPE: PRT
<213> ORGANISM: Artificial Sequence
<220> FEATURE:
<223> OTHER INFORMATION: gp100 25 peptide

<400> SEQUENCE: 28

Glu Gly Ser Arg Asn Gln Asp Trp Leu
1               5

<210> SEQ ID NO 29
<211> LENGTH: 9
<212> TYPE: PRT
<213> ORGANISM: Artificial Sequence
<220> FEATURE:
<223> OTHER INFORMATION: MAGE 1 nonapeptide

<400> SEQUENCE: 29

Glu Ala Asp Pro Thr Gly His Ser Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: MART-APL peptide

<400> SEQUENCE: 30

Leu Ala Gly Ile Gly Ile Leu Thr Val
1               5

<210> SEQ ID NO 31
<211> LENGTH: 9
<212> TYPE: PRT
<213> ORGANISM: Artificial Sequence
<220> FEATURE:
<223> OTHER INFORMATION: natural peptide

<400> SEQUENCE: 31

Ala Ala Gly Ile Gly Ile Leu Thr Val
1               5
```

```
<210> SEQ ID NO 32
<211> LENGTH: 10
<212> TYPE: PRT
<213> ORGANISM: Artificial Sequence
<220> FEATURE:
<223> OTHER INFORMATION: PSA-1 peptide

<400> SEQUENCE: 32

Phe Leu Thr Pro Lys Lys Leu Gln Cys Val
1               5                   10
```